United States Patent
Zhang et al.

(10) Patent No.: US 9,855,366 B2
(45) Date of Patent: Jan. 2, 2018

(54) ENERGY-PROVIDING BONE-REPAIR DEGRADABLE POROUS SCAFFOLD, PREPARATION METHOD THEREOF, AND APPLICATION THEREOF

(71) Applicant: HUAZHONG UNIVERSITY OF SCIENCE AND TECHNOLOGY, Wuhan (CN)

(72) Inventors: Shengmin Zhang, Wuhan (CN); Mingle Cai, Wuhan (CN); Haoming Liu, Wuhan (CN)

(73) Assignee: Huazhong University of Science and Technology, Wuhan (CN)

( * ) Notice: Subject to any disclaimer, the term of this patent is extended or adjusted under 35 U.S.C. 154(b) by 97 days.

(21) Appl. No.: 15/130,361

(22) Filed: Apr. 15, 2016

(65) Prior Publication Data

US 2017/0246343 A1    Aug. 31, 2017

Related U.S. Application Data

(60) Provisional application No. 62/317,252, filed on Apr. 1, 2016.

(30) Foreign Application Priority Data

Feb. 26, 2016  (CN) .......................... 2016 1 0108128

(51) Int. Cl.
    *A61L 27/18*    (2006.01)
    *A61L 27/22*    (2006.01)
    *A61L 27/54*    (2006.01)
    *A61L 27/58*    (2006.01)
    *A61L 27/56*    (2006.01)

(52) U.S. Cl.
    CPC ............. *A61L 27/18* (2013.01); *A61L 27/222* (2013.01); *A61L 27/54* (2013.01); *A61L 27/56* (2013.01); *A61L 27/58* (2013.01); *A61L 2300/412* (2013.01); *A61L 2300/604* (2013.01); *A61L 2430/02* (2013.01)

(58) Field of Classification Search
    CPC ........ A61L 27/18; A61L 27/222; A61L 27/54; A61L 27/58; A61L 27/56; A61L 2430/02; A61L 2300/412; A61L 2300/604
    See application file for complete search history.

*Primary Examiner* — Trevor Love
(74) *Attorney, Agent, or Firm* — Kolisch Hartwell, P.C.

(57) ABSTRACT

The invention discloses an energy-providing bone-repair degradable porous scaffold, a preparation method thereof, and an application thereof. The invention obtains an energy-based biomaterial solution by compositing gelatin, a polyatomic acid and derivatives thereof, a dibasic alcohol and derivatives thereof, and a tribasic alcohol and derivatives thereof in a chemical cross-linking manner by using diisocyanate, and further obtains a porous scaffold through a drying method. The porous scaffold can avoid the problem of an acidic microenvironment caused by in vivo implantation of the existing biomaterial and keep the activity of an osteoblast cell, thereby improving the rate of repairing the damaged bone tissue with the energy-based biomaterial. The porous scaffold of the invention can be used as a filling material for bone repair in a surgical operation.

6 Claims, 1 Drawing Sheet

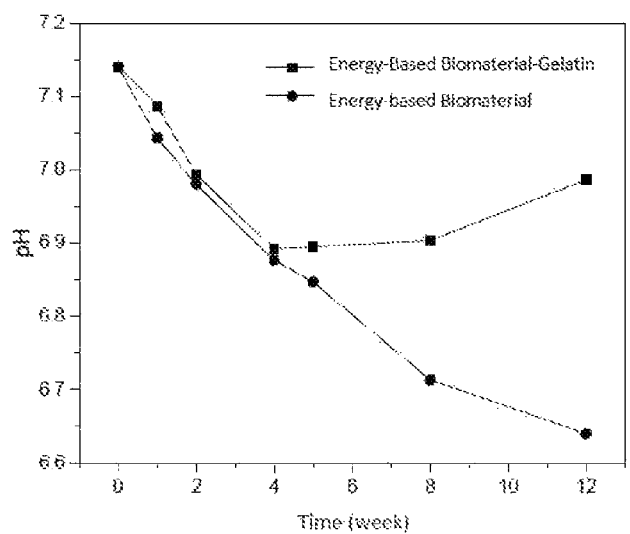

ENERGY-PROVIDING BONE-REPAIR DEGRADABLE POROUS SCAFFOLD, PREPARATION METHOD THEREOF, AND APPLICATION THEREOF

CROSS-REFERENCES TO RELATED APPLICATIONS

This application claims priority to Chinese Patent Application No. 201610108128.9 filed Feb. 26, 2016 and U.S. Provisional Application No. 62/317,252 filed Apr. 1, 2016, of which the full disclosure of this application is incorporated herein by reference for all purposes.

FIELD OF THE INVENTION

The invention relates to the field of biomaterials and tissue engineering technology, and particularly to an energy-providing bone-repair degradable porous scaffold, a preparation method thereof, and an application thereof.

BACKGROUND OF THE INVENTION

An important respect of biomedical engineering is researching of scaffold materials. Introducing an appropriate scaffold material is an important factor for facilitating differentiation of a cell along a desired direction and thus the formation of a tissue, which is beneficial for tissue repairing. A three-dimensional porous cell scaffold can not only accommodate a cell, a cell product and an extracellular matrix, but also be a basic cell attachment frame and a metabolism site, the morphology and functionality of which can directly affect the morphology and functionality of a tissue formed therefrom.

Bone injury and bone defect are clinically common, and the injured bone can be repaired with an endogenous bone or an exogenous bone. However, both the endogenous and exogenous bones have disadvantages such as a damage of reoperation to a patient, and thus recently there are many researches of bone tissue engineering. The scaffold material plays an important role in the bone tissue engineering, which provides a three-dimensional scaffold for cell growth and tissue repair. A desired material of a bone tissue engineering scaffold should have the following five features: (1) good biocompatibility, no cytotoxicity during in vitro culture, no inflammation and rejection reaction caused when implanted in vivo; (2) a three-dimensional structure, an appropriate porosity and aperture size, which are beneficial for cell growth, transportation of nutrients and discharge of metabolic products; (3) a good surface activity, and suitability to cell adhesion and proliferation; (4) a good degradation performance, wherein the scaffold should be gradually degraded and absorbed during tissue formation and does not affect the structure and function of a cambium; and (5) mouldability, wherein the material can be processed into a desired shape and maintain a certain mechanical strength.

Currently, the research of the porous composite scaffold mainly focuses on the composition between a biodegradable polymer and a ceramic particle having a biological activity. A biodegradable polymer (such as poly L-lactic acid (PLLA) and polycaprolactone (PCL)) has good biocompatibility, biodegradability, a great mechanical property, a controllable degradability and processibility, and a degraded product of the polymer can participate in human metabolism. This makes them become one of important materials used currently in the biomedical field, and has been approved by U.S. Food and Drug Administration (FDA) for human use.

However, carboxylic acid generated by degradation of a polyester polymer scaffold such as polylactic acid, polycaprolactone and polylactic acid-hydroxyacetic acid copolymer causes pH reduction in a tissue microenvironment, which is unfavorable for cell growth and angiogenesis (Sung H J, Meredith C, Johnson C, et al. The effect of scaffold degradation rate on three-dimensional cell growth and angiogenesis. Biomaterials, 2004, 25: 5735-5742.); and when the scaffold size is too large or the body fluid circulation at the implanted site is relatively weak, since the acidic materials generated by degradation is not buffered with enough body fluid, pH is reduced significantly, which is a hinder to the conduction of bone repair (Agrawal C M, Athanasiou K A. Technique to control pH in vicinity of biodegrading PLA-PGA implants. Journal of biomedical materials research, 1997, 38: 105-114.). Through further research, it is found that compared with that under normal physiological conditions, when pH is below 6.5 the activity of an osteoblast cell is reduced greatly (Shen Y, Liu W, Wen C, et al. Bone regeneration: importance of local pH—strontium-doped borosilicate scaffold. Journal of Materials Chemistry, 2012, 22: 8662-8670.), wherein since the osteoblast cell is used for generating new bone, avoiding a too low pH during the bone repair process is beneficial for maintaining the activity of the osteoblast cell, thereby facilitating the repair and regeneration of a bone tissue.

SUMMARY OF THE INVENTION

In order to solve the aforementioned problems in the prior art, a main object of the invention is to provide an energy-providing degradable porous scaffold for bone-tissue repair and regeneration, a preparation method thereof and an application thereof, thereby solving the problem that a local microenvironment tends to be acidic during the in vivo degradation process of existing energy-based biomaterials, and improving the rate of repairing the damaged bone tissue with the energy-based biomaterial.

A method for preparing an energy-providing bone-repair degradable porous scaffold includes the following steps:

(1) mixing a polyatomic acid and derivatives thereof, a dibasic alcohol and derivatives thereof, and a tribasic alcohol and derivatives thereof by a molar ratio of $1:x:(1-x)$, with x between 0 and 1, reacting under stirring at 100-160° C. for 0.5-3 hours, adding an entrainer once in a while, continuing the reaction under a vacuum degree from −80 kPa to −95 kPa for 0.5-10 hours, collecting the products, and adding a polar solvent to make up a first solution of 1-50 wt %;

(2) adding a diisocyanate cross-linking agent at an amount of 0.01-0.2 mL per milliliter of the first solution, reacting at 50-100° C. for 0.1-1 hour, adding a gelatin solution of 1-50 wt % and well-mixing to obtain a second solution, wherein the added gelatin solution is 0.1-10 times as volume as the first solution;

(3) adding a pore-forming agent with a diameter of 100-900 μm into a mould, and pouring the second solution obtained in step (2) into the mould; and (4) removing the pore-forming agent after curing, and obtaining a porous scaffold by using a drying method, wherein, the polyatomic acid and derivatives thereof are one or more selected from succinic acid, citric acid, isocitric acid, fumaric acid, malic acid, cis-aconitic acid, ketoglutaric acid and oxaloacetic acid; the dibasic alcohol and derivatives thereof are one or more selected from glycol, glycol diacetate, butanediol, propanediol, hexanediol and poly(ethylene glycol); and the tribasic alcohol and derivatives thereof are one or more selected from glycerine and glycidol.

As used herein, weight percentage (wt %) is a weight ratio of a solute to a solution.

In certain embodiments, the polyatomic acid and derivatives thereof are succinic acid; the dibasic alcohol and derivatives thereof are glycol; and the tribasic alcohol and derivatives thereof are glycerine.

In certain embodiments, in step (1), the entrainer is toluene, xylene or benzene, and the entrainer is added at an amount of 10 mL every 0.5 hours.

In certain embodiments, in step (1), the polar solvent is tetrahydrofuran, acetone or dimethylformamide.

In further embodiment, in step (1), the entrainer is toluene and the polar solvent is acetone.

In certain embodiments, in step (2) the diisocyanate is hexamethylene diisocyanate, L-lysine diisocyanate or toluene-2,4-diisocyanate.

In certain embodiments, in step (2), the gelatin solution is a solution of gelatin in dimethyl sulfoxide or hexafluoroisopropanol.

In further embodiment, in step (2), the diisocyanate is hexamethylene diisocyanate and the gelatin solution is a solution of gelatin in dimethyl sulfoxide.

In certain embodiments, in step (3), the pore-forming agent is a sodium chloride particle or sugar ball.

In further embodiment, in step (3), the particle of the pore-forming agent is removed by soaking in deionized water after being cured at 80° C. for 12 hours.

In certain embodiments, in step (4), the drying method is freeze drying, drying in an oven or drying at a room temperature.

In certain embodiments, the molecular weight of the gelatin is 10,000-400,000 dalton, and amino acids constituting the gelatin are selected from arginine, lysine, histidine, glycine, alanine, proline, 4-hydroxyproline and/or other amino acids.

An energy-providing bone-repair degradable porous scaffold is prepared with the aforementioned preparation method.

In certain embodiments, a porosity of the porous scaffold is 50-99%, pore size is 100-900 μm, and compression modulu is 0.1-10 MPa.

An energy-providing bone-repair degradable porous scaffold prepared with the aforementioned preparation method can be applied as a material used for bone-tissue repair and regeneration.

The benefit effects of the present invention are:

1. The energy-based biomaterial formed through the preparation method of the invention can generate a series of bioactive molecules, so as to provide energy for tissue cells.

2. The porous scaffold through further preparation of the energy-based material obtained by implementing the method of the invention has a good biocompatibility, and while the tissue repair function thereof is exerted, along with the continuous conduction of the degradation process of the scaffold itself, the degraded products enter a cell continuously, so as to exert a function in the cell in an energy-providing manner, thereby facilitating cell growth, cell proliferation and tissue repair.

3. In the invention, by adding the gelatin into the energy-based biomaterial through a reaction, the degradation rate of the scaffold can be adjusted, and the pH during the degradation process is controlled within an appropriate range. I-type collagen is one of main organic components of a bone, and gelatin is a part of hydrolyzate of a collagen, particularly of the I-type collage. Gelatin is a degradable polymer with a good biocompatibility, which is widely applied in a plasma compatibilizer, a surgical biomaterial and a drug carrier. For the amino acids constituting the gelatin, the number of basic amino acids such as arginine, lysine and histidine is 1.5 times of the number of acidic amino acids, such that the degraded products of gelatin are basic in whole. The gelatin is composited with the energy-based biomaterial in an appropriate proportion, such that while the polyester polyurethane is degraded to release acidic materials, the degraded products of gelatin act for balancing the acidic materials, so as to avoid a too low pH. Furthermore, the bone repair process is accompanied with generation of new collagen, and thus a supply of amino acids is desired. The amino acids generated by the degradation of gelatin derived from the collagen can supply raw materials for the synthesis of new collagen.

4. The porous scaffold formed by the preparation method of the invention can be used as a filling material for bone repair in a surgical operation, so as to avoid the problem of an acidic microenvironment caused by in vivo implantation of the material and keep the activity of an osteoblast cell, thereby improving the rate of repairing the damaged bone tissue with the energy-based biomaterial.

BRIEF DESCRIPTION OF THE DRAWINGS

FIG. 1 is a curve comparison diagram of pH variation of a phosphate buffered solution over time when the energy-based biomaterial-gelatin porous scaffold according to an example of the application and an energy-based biomaterial porous scaffold containing no gelatin are degraded in the solution.

DETAILED DESCRIPTION OF THE INVENTION

To solve the problem that a local microenvironment tends to be acidic during the in vivo degradation process of existing energy-based biomaterials, the invention discloses an energy-providing degradable porous scaffold for bone-tissue repair and regeneration, a preparation method thereof and an application thereof, which keep the activity of an osteoblast cell and improve the rate of repairing the damaged bone tissue with the energy-based biomaterial.

For better understanding of the aforementioned technical solution, the aforementioned technical solution is illustrated hereafter in detail in connection with specific examples.

A method for preparing an energy-providing bone-repair degradable porous scaffold is provided by examples of the application, which includes the following steps:

(1) mixing a polyatomic acid and derivatives thereof, a dibasic alcohol and derivatives thereof, and a tribasic alcohol and derivatives thereof by a molar ratio of 1:x:(1−x), with x between 0 and 1, reacting under stirring at 100-160° C. for 0.5-3 hours, adding an entrainer once in a while, continuing the reaction under a vacuum degree from −80 kPa to −95 kPa for 0.5-10 hours, collecting the products, and adding a polar solvent to make up a first solution of 1-50 wt %;

(2) adding a diisocyanate cross-linking agent at an amount of 0.01-0.2 mL per milliliter of the first solution, reacting at 50-100° C. for 0.1-1 hour, adding a gelatin solution of 1-50 wt % and well-mixing to obtain a second solution, wherein the added gelatin solution is 0.1-10 times as volume as the first solution;

(3) adding a pore-forming agent with a diameter of 100-900 μm into a mould, and pouring the second solution obtained in step (2) into the mould; and (4) removing the pore-forming agent after curing, and obtaining a porous scaffold by using a drying method, wherein the polyatomic acid and derivatives thereof are one or more selected from succinic acid, citric acid, isocitric acid, fumaric acid, malic acid, cis-aconitic acid, ketoglutaric acid and oxaloacetic acid; the dibasic alcohol and derivatives thereof are one or more selected from glycol, glycol diacetate, butanediol, propanediol, hexanediol and poly(ethylene glycol); and the tribasic alcohol and derivatives thereof are one or more selected from glycerine and glycidol.

As used herein, weight percentage (wt %) is a weight ratio of a solute to a solution.

In step (1), the entrainer is toluene, xylene or benzene, and the entrainer is added at an amount of 10 mL every 0.5 hours.

In step (1), the polar solvent is tetrahydrofuran, acetone or dimethylformamide.

In step (2), the diisocyanate is hexamethylene diisocyanate, L-lysine diisocyanate or toluene-2,4-diisocyanate.

In step (2), the gelatin solution is a solution of gelatin in dimethyl sulfoxide or hexafluoroisopropanol.

In step (3), the pore-forming agent is a sodium chloride particle or sugar ball.

In step (3), the particle of the pore-forming agent is removed by soaking in deionized water after being cured at 80° C. for 12 hours.

In step (4), the drying method is freeze drying, drying in an oven or drying at a room temperature.

The molecular weight of the gelatin is 10,000-400,000 dalton, and amino acids constituting the gelatin are selected from arginine, lysine, histidine, glycine, alanine, proline, 4-hydroxyproline and/or other amino acids.

For the energy-providing bone-repair degradable porous scaffold prepared through the aforementioned preparation method according to the examples of the application, a porosity of the porous scaffold is 50-99%, pore size is 100-900 μm, and compression modulu is 0.1-10 MPa.

The energy-providing bone-repair degradable porous scaffold prepared through the aforementioned preparation method according to the examples of the application can be applied as a material used for bone-tissue repair and regeneration.

EXAMPLES

Example 1

5.90 g succinic acid, 0.56 mL glycol and 2.90 mL glycerine were mixed, reacted under stirring at 140° C. for 3 hours, and 10 mL toluene was added every 0.5 hours. The reaction was continued at a vacuum degree of −80 kPa for 10 hours to collect obtained products, and the products were made up into an acetone solution of 30 wt %. 0.5 mL of the solution was taken, into which 35 μL hexamethylene diisocyanate was added to react at 100° C. for 0.1 hours. 1 mL gelatin/dimethyl sulfoxide solution of 15 wt % was added and well-mixed, and the mixed solution was poured into a mould filled with 200 μm solid sodium chloride particles to be cured at 80° C. for 12 hours, then the sodium chloride was removed by soaking in deionized water, and finally the desired porous scaffold was obtained by using a freeze drying method. The porosity of the porous scaffold was 80%, pore size was 200 μm, and compression modulu was 1 MPa.

Rat mesenchymal stem cells were cultured on the porous scaffold of example 1, and a week later by detecting the number of living cells with a CCK-8 agent it was found that the cells grew well, which demonstrated that this scaffold material had good cell compatibility.

FIG. 1 is a curve diagram of pH variation of a phosphate buffered solution over time when the energy-based biomaterial-gelatin porous scaffold obtained from example 1 is degraded in the solution, wherein compared with an energy-based biomaterial porous scaffold containing no gelatin, when degraded, the energy-based biomaterial-gelatin porous scaffold obtained from example 1 can avoid the problem of a too low pH.

Example 2

5.90 g succinic acid, 1.10 mL glycol and 2.20 mL glycerine were mixed, reacted under stirring at 150° C. for 2.5 hours, and 10 mL toluene was added every 0.5 hours. The reaction was continued at a vacuum degree of −90 kPa for 8 hours to collect obtained products, and the products were made up into an acetone solution of 20 wt %. 0.5 mL of the solution was taken, into which 43 μL hexamethylene diisocyanate was added to react at 90° C. for 0.15 hours. 2 mL gelatin/dimethyl sulfoxide solution of 10 wt % was added and well-mixed, and the mixed solution was poured into a mould filled with 300 μm solid sodium chloride particles to be cured at 80° C. for 12 hours, then the sodium chloride was removed by soaking in deionized water, and finally the desired porous scaffold was obtained by using a freeze drying method. The porosity of the porous scaffold was 70%, pore size was 300 μm, and compression modulu was 5 MPa.

Example 3

5.90 g succinic acid, 0.28 mL glycol and 3.30 mL glycidol were mixed, reacted under stirring at 160° C. for 2 hours, and 10 mL toluene was added every 0.5 hours. The reaction was continued at a vacuum degree of −95 kPa for 6 hours to collect obtained products, and the products were made up into an acetone solution of 30 wt %. 1 mL of the solution was taken, into which 62 μL hexamethylene diisocyanate was added to react at 80° C. for 0.25 hours. 1 mL gelatin/dimethyl sulfoxide solution of 15 wt % was added and well-mixed, and the mixed solution was poured into a mould filled with 200 solid μm sodium chloride particles to be cured at 80° C. for 12 hours, then the sodium chloride was removed by soaking in deionized water, and finally the desired porous scaffold was obtained by using a freeze drying method. The porosity of the porous scaffold was 90%, pore size was 200 μm, and compression modulu was 8 MPa.

Example 4

5.90 g citric acid, 0.56 mL butanediol and 2.90 mL glycerine were mixed, reacted under stirring at 140° C. for 3 hours, and 10 mL toluene was added every 0.5 hours. The reaction was continued at a vacuum degree of −80 kPa for 10 hours to collect obtained products, and the products were made up into a tetrahydrofuran solution of 30 wt %. 0.5 mL of the solution was taken, into which 35 μL L-lysine diisocyanate was added to react at 100° C. for 0.1 hours. 1 mL gelatin/dimethyl sulfoxide solution of 15 wt % was added and well-mixed, and the mixed solution was poured into a mould filled with 200 μm solid sodium chloride particles to be cured at 80° C. for 12 hours, then the sodium chloride was removed by soaking in deionized water, and finally the desired porous scaffold was obtained by using a freeze drying method. The porosity of the porous scaffold was 85%, pore size was 200 μm, and compression modulu was 2 MPa.

Example 5

5.90 g oxaloacetic acid, 1.10 mL propanediol and 2.20 mL glycerine were mixed, reacted under stirring at 150° C. for 2.5 hours, and 10 mL toluene was added every 0.5 hours. The reaction was continued at a vacuum degree of −90 kPa for 8 hours to collect obtained products, and the products were made up into a dimethylformamide solution of 20 wt %. 0.5 mL of the solution was taken, into which 43 μL toluene-2,4-diisocyanate was added to react at 90° C. for 0.15 hours. 2 mL gelatin/hexafluoroisopropanol solution of 10 wt % was added and well-mixed, and the mixed solution was poured into a mould filled with 300 μm sugar balls to be cured at 80° C. for 12 hours, then the sugar balls were removed by soaking in deionized water, and finally the desired porous scaffold was obtained by drying in an oven. The porosity of the porous scaffold was 78%, pore size was 300 μm, and compression modulu was 10 MPa.

Example 6

5.90 g malic acid, 0.28 mL hexanediol and 3.30 mL glycerine were mixed, reacted under stirring at 160° C. for 2 hours, and 10 mL toluene was added every 0.5 hours. The reaction was continued at a vacuum degree of −95 kPa for 6 hours to collect obtained products, and the products were made up into a tetrahydrofuran solution of 30 wt %. 1 mL of the solution was taken, into which 62 μL hexamethylene diisocyanate was added to react at 80° C. for 0.25 hours. 1 mL gelatin/hexafluoroisopropanol solution of 15 wt % was added and well-mixed, and the mixed solution was poured into a mould filled with 200 μm sugar balls to be was cured at 80° C. for 12 hours, then the sugar balls were removed by soaking in deionized water, and finally the desired porous scaffold was obtained by drying at a room temperature. The porosity of the porous scaffold was 68%, pore size was 200 μm, and compression modulu was 3 MPa.

The technical solution provided by the aforementioned examples of the application at least has the following technical effects or advantages:

1. The energy-based biomaterial formed through the preparation method of the example of the application can generate a series of bioactive molecules, so as to provide energy for tissue cells.

2. The porous scaffold through further preparation of the energy-based material obtained by implementing the method of the example of the application has a good biocompatibility, and while the tissue repair function thereof is exerted, along with the continuous conduction of the degradation process of the scaffold itself, the degraded products enter a cell continuously, so as to exert a function in the cell in an energy-providing manner, thereby facilitating cell growth, proliferation and tissue repair;

3. In the example of the application, by adding the gelatin into the energy-based biomaterial through a reaction, the degradation rate of the scaffold can be adjusted, and the pH during the degradation process is controlled within an appropriate range. I-type collagen is one of main organic components of a bone, and gelatin is a partially hydrolyzate of a collagen, particularly of the I-type collagen. Gelatin is a degradable polymer with a good biocompatibility, which is widely applied in a plasma compatibilizer, a surgical biomaterial and a drug carrier. For the amino acids constituting the gelatin, the number of basic amino acids such as arginine, lysine and histidine is 1.5 times of the number of acidic amino acids, such that the degraded products of gelatin are basic in whole. The gelatin is composited with the energy-based biomaterial in an appropriate proportion, such that while the polyester polyurethane is graded to release acidic materials, the degraded products of gelatin act for balancing the acidic materials, so as to avoid a too low pH. Furthermore, the bone repair process is accompanied with generation of new collagen, and thus a supply of amino acids is desired. The amino acids generated by the degradation of gelatin derived from the Collagen can supply raw materials for the synthesis of new collagen.

4. The porous scaffold formed by the preparation method of the application of the application can be used as a filling material for bone repair in a surgical operation, so as to avoid the problem of an acidic microenvironment caused by in vivo implantation of the material and keep the activity of an osteoblast cell, thereby improving the rate of repairing the damaged bone tissue with the energy-based biomaterial.

Although the preferred embodiments of the invention are described, it should be understood that once the basic creative concepts are known by a person skilled in the art, further changes and modifications can be made to these embodiments. Therefore, the appended claims are intended to be interpreted as including the preferred embodiments and all the changes and modifications falling within the scope of the invention. Obviously, a person skilled in the art can make various changes and modifications to the invention without departing from the spirit and scope of the invention. As such, if these modifications and variations of the invention are within the scope of the claims of the invention and equivalent techniques thereof, then the invention is intended to encompass these modifications and variations.

REFERENCES

1. Sung H J, Meredith C, Johnson C, et al. The effect of scaffold degradation rate on three-dimensional cell growth and angiogenesis. Biomaterials, 2004, 25: 5735-5742.
2. Agrawal C M, Athanasiou K A. Technique to control pH in vicinity of biodegrading PLA-PGA implants. Journal of biomedical materials research, 1997, 38: 105-114.
3. Shen Y, Liu W, Wen C, et al. Bone regeneration: importance of local pH—strontium-doped borosilicate scaffold. Journal of Materials Chemistry, 2012, 22: 8662-8670.

The invention claimed is:

1. A method for preparing an energy-providing bone-repair degradable porous scaffold, comprising the following steps:
(1) mixing a polyatomic acid or derivatives thereof, a dibasic alcohol or derivatives thereof, and a tribasic alcohol or derivatives thereof by a molar ratio of 1:x:(1−x), with x between 0 and 1, reacting under stirring at 100-1600 C for 0.5-3 hours, adding an entrainer, which is toluene, xylene or benzene, at an amount of 10 mL every 0.5 hours continuing the reaction under a vacuum degree from −80 kPa to −95 kPa for 0.5-10 hours, collecting the products, and adding a polar solvent, which is tetrahydrofuran, acetone or dimethylformamide, to make up a first solution of 1-50 wt %;

(2) adding a diisocyanate cross-linking agent at an amount of 0.01-0.2 mL per milliliter of the first solution, reacting at 50-100 C for 0.1-1 hour, adding a gelatin solution of 1-50 wt % and well-mixing to obtain a second solution, wherein the added gelatin solution is 0.1-10 times as volume as the first solution;

(3) adding a pore-forming agent with a diameter of 100-900 pm into a mould, and pouring the second solution obtained in step (2) into the mould; and (4) removing the pore-forming agent after curing, and obtaining a porous scaffold by using a drying method, wherein, the polyatomic acid or derivatives thereof are one or more selected from succinic acid, citric acid, isocitric acid, fumaric acid, malic acid, cis-aconitic acid, ketoglutaric acid and oxaloacetic acid; the dibasic alcohol or derivatives thereof are one or more selected from glycol, glycol diacetate, butanediol, propanediol, hexanediol and poly(ethylene glycol); and the tribasic alcohol or derivatives thereof are one or more selected from glycerine and glycidol.

2. The method for preparing an energy-providing bone-repair degradable porous scaffold of claim 1, wherein the polyatomic acid or derivatives thereof are succinic acid; the dibasic alcohol or derivatives thereof are glycol; and the tribasic alcohol or derivatives thereof are glycerine.

3. The method for preparing an energy-providing bone-repair degradable porous scaffold of claim 1, wherein, in step (2), the diisocyanate is hexamethylene diisocyanate, L-lysine diisocyanate or toluene-2,4-diisocyanate; and the gelatin solution is a solution of gelatin in dimethyl sulfoxide or hexafluoroisopropanol.

4. The method for preparing an energy-providing bone-repair degradable porous scaffold of claim 1, wherein, in step (3), the pore-forming agent is a sodium chloride particle or sugar ball, and the particle of the pore-forming agent is removed by soaking in deionized water after being cured at 80° C. for 12 hours.

5. The method for preparing an energy-providing bone-repair degradable porous scaffold of claim 1, wherein, in step (4), the drying method is freeze drying, drying in an oven or drying at a room temperature.

6. The method for preparing an energy-providing bone-repair degradable porous scaffold of claim 1, wherein the molecular weight of the gelatin is 10,000-400,000 dalton, and amino acids constituting the gelatin are selected from arginine, lysine, histidine, glycine, alanine, proline and/or 4-hydroxyproline.

* * * * *